(12) United States Patent
Egan et al.

(10) Patent No.: US 6,522,975 B1
(45) Date of Patent: Feb. 18, 2003

(54) PREDICTION OF MOLECULAR POLAR SURFACE AREA AND BIOABSORPTION

(75) Inventors: William J. Egan, Burlington, NJ (US); Giorgio Lauri, Wynnewood, PA (US)

(73) Assignee: Pharmacopeia, Inc., Cranbury, NJ (US)

(*) Notice: Subject to any disclaimer, the term of this patent is extended or adjusted under 35 U.S.C. 154(b) by 0 days.

(21) Appl. No.: 09/552,549

(22) Filed: Apr. 19, 2000

(51) Int. Cl.$^7$ .......................... G01N 33/48; G01N 15/00
(52) U.S. Cl. .......................... 702/19; 702/22; 702/27; 702/30; 422/68.1
(58) Field of Search .......................... 702/19, 22, 27, 702/30; 395/500.23; 422/68.1

(56) References Cited

PUBLICATIONS

Van de Waterbeemd et al.; "Estimation of Blood–Brain Barrier Crossing of Drugs Using Molecular Size and Shape, and H–Bonding Descriptors." Journal of Drug Targeting, 1998, vlol. 6, No. 2, pp. 151–165.*

Egan et al.; "Prediction of Drug Absorption Using Multivariate Statistics." Journal of Medicinal Chemistry, 2000, vol. 43, pp. 3867–3877.*

Egan et al.; "Outlier Detection i Multivariate Analytical Chemical Data." Analytical Chemistry, 1998, vol. 70, pp. 2372–2379.*

Ghose, et al., J. Phys. Chem. A, vol. 102, pp. 3762–3772, 1998 "Prediction of Hydrophobic (Lipophilic) Properties of Small Organic Molecules Using Fragmental Methods: An Anlaysis of ALOGP and CLOGP Methods".

Hall, et al., J. Chem. Inf. Comput. Sci., vol. 35, pp. 1039–1045, 1995 "Electrotopological State Indices for Atom Types: A Novel Combination of Electronic, Topoloical, and Valence State Information".

Winiwarter, et al., J. Med. Chem., vol. 41, pp. 4939–4949, 1998 "Correlation of Human Jejunal Permeability (in Vivo) of Drugs with Experimentally and Theoretically Derived Parameters A Multivariate Data Analysis Approach".

Kier, et al., Pharmaceutical Research, vol. 7, No. 8, pp. 801–807, 1990 "An Electrotopological–State Index for Atoms in Molecules".

David E. Clark, Journal of Pharmaceutical Sciences, vol. 88, No. 8, pp. 807–814, Aug. 1999 "Rapid Calculation of Polar Molecular Surface Area and Its Application to the Prediction of Transport Phenomena. 1. Prediction of Intestinal Absorption".

Camenisch, et al., European Journal of Pharmaceutical Sciences, vol. 6, pp. 313–319, 1998 "Estimation of permeability by passive diffusion through Caco–2 cell monolayers using the drugs' lipophilicity and molecular weight".

Palm, et al., J. Med. Chem., vol. 41, pp. 5382–5392, 1998 "Evaluation of Dynamic Polar Molecular Surface Area as Predictor of Drug Absorption: Comparison with Other Computational and Experimental Predictors".

van de Waterbeemd, et al., Quant. Struct–Act. Relat. vol. 15, pp. 480–490, 1996 "Estimation of Caco–2 Cell Permeability using Calculated Molecular Descriptors".

(List continued on next page.)

Primary Examiner—Ardin H. Marschel
Assistant Examiner—Monika Sheinberg
(74) Attorney, Agent, or Firm—Knobbe, Martens, Olson & Bear LLP (57) ABSTRACT

The polar surface area of molecules is computed without reference to three dimensional molecular structures using a linear equation incorporating counts of nitrogens, oxygens, and related atom clusters. Methods and systems for predicting intestinal absorption of candidate compounds use the polar surface area and the octanol/water partition coefficient as descriptors.

6 Claims, 5 Drawing Sheets

OTHER PUBLICATIONS

Wessel, et al., *J. Chem. Inf. Comput. Sci.*, vol. 38, pp. 726–735, 1998 "Prediction of Human Intestinal Absorption of Drug Compounds from Molecular Structure".

Wils, et al., *The Journal Of Pharmacology And Experimental Therapeutics*, vol. 269, No. 2, pp. 654–658, 1994 "High Lipophilicity Decreases Drug Transport Across Intestinal Epithelial Cells[1]".

Palm, et al., *Pharmaceutical Research*, vol. 14, No. 5, pp.568–571, 1997 "Polar Molecular Surface Properties Predict the Intestinal Absorption of Drugs in Humans".

Stenberg, et al., *Pharmaceutical Research*, vol. 16, No. 2, pp. 205–212, 1999 "Prediction of Membrane Permeability to Peptides from Calculated Dynamic Molecular Surface Properties".

Norinder, et al., *European Journal Of Pharmaceutical Sciences*, vol. 8, pp. 49–56, 1999 "Theoretical calculation and prediction of intestinal absorption of drugs in humans using MolSurf parametrization and PLS statistics".

David E. Clark, *Journal of Pharmaceutical SCiences*, vol. 88, No. 8, pp. 815–821, Aug. 1999 "Rapid Calculation of Polar Molecular Surface Area and Its Application to the Prediction of Transport Phenomena. 2. Prediction of Blood–Brain Barrier Penetration".

\* cited by examiner

PREDICTION OF MOLECULAR POLAR SURFACE AREA AND BIOABSORPTION

SUMMARY OF THE INVENTION

1. Field of the Invention

The invention relates to computational methods of pharmaceutical discovery. Specifically, the invention relates to the prediction of membrane permeability and physiological absorption of molecules.

2. Description of the Related Art

In the development of pharmaceutical compounds, it is well known that identifying a compound with a desired biological activity is not itself sufficient to determine that compound's suitability as a drug. Not only must the compound exhibit the necessary biological activity, but it must also be deliverable to the target tissue(s), preferably in a cost effective and convenient manner such as oral administration. This has been a problem with several treatment protocols. For example, a wide variety of peptide molecules have been shown to have useful pharmacological activity, but their generally limited capacity to diffuse through biomembranes such as the human gastrointestinal epithelium has limited their clinical development. Effective oral administration requires that a drug be absorbed through the intestinal membranes to enter systemic circulation and if such absorption is limited, a compound's promise for clinical development is poor.

Not only is intestinal absorption an important concern during drug development, but the ability of a candidate compound to penetrate the blood-brain barrier is also of significant interest. The blood-brain barrier (BBB) is a cellular system that separates the fluids of the central nervous system from the circulatory system. Drugs intended for targets in the central nervous system should be able to penetrate the BBB. On the other hand, drugs intended for other target tissues may cause unwanted side effects if they freely pass into the fluids of the central nervous system.

In vivo animal testing for bioabsorption and blood-brain barrier penetration has long been practiced. In addition, a cell based in vitro assay using human intestinal caco-2 cells is in widespread use to measure the biomembrane permeability of drug candidate compounds. Because both of these protocols are slow, expensive, and labor intensive, computational methods to predict the potential for gastrointestinal absorption and blood-brain barrier penetration based on more easily obtained molecular characteristics have been developed. Also, such computational methods are of great interest for the in silico prediction of absorption and blood-brain barrier penetration for virtual libraries of compounds which have not been synthesized, for the purposes of determining which compounds should be synthesized. In these computational models, a formula for estimating either the % human intestinal absorption (%HIA) or the logarithm of the steady state ratio of the compound's concentration in the central nervous system and the blood (often called logBB) is constructed. The formula typically uses molecular properties and parameters that may be derived from the molecular structure of the compound. Using these formulas, %HIA and logBB may be estimated without the need to perform in vivo experiments.

Many models focus on molecular characteristics related to hydrogen bonding, lipophilicity, and molecular weight to predict propensity for intestinal absorption or blood-brain barrier penetration. A sigmoidal relationship between the polar surface area (PSA) of a molecule and its %HIA has been observed, with high polar surface area correlated to low %HIA. This is shown in Palm, et al. Polar Molecular Surface Properties Predict the Intestinal Absorption of Drugs in Humans, *Pharmaceutical Research*, Vol. 14, No. 5, p. 568 (1997). It has also been observed that molecules having either especially high or especially low octanol/water partition coefficients (logP), which is a measure of lipophilicity, are associated with low %HIA. Palm, supra, and Wils, et al., High Lipophilicity Decreases Drug Transport Across Intestinal Epithelial Cells, *The Journal of Pharmacology and Experimental Therapeutics*, Volume 269, No. 2, p. 654 (1994). The disclosures of both the Palm and Wils articles are hereby incorporated by reference in their entireties.

Accordingly, molecular PSA has been suggested as a parameter which can be used to distinguish between well absorbed and poorly absorbed compounds, with 140 square angstroms being proposed as a cutoff value. Clark, Rapid Calculation of Polar Molecular Surface Area and its Application to the Prediction of Transport Phenomena 1. Prediction of Intestinal Absorption, *Journal of Pharmaceutical Sciences*, Vol. 88, No. 8, p. 807 (1999). PSA has also been used as a variable in linear formulas for predicting membrane permeability and logBB. In some cases, logP is used along with PSA in such linear formulas. Clark, Rapid Calculation of Polar Molecular Surface Area and its Application to the Prediction of Transport Phenomena 2. Prediction of Blood-Brain Barrier Penetration, *Journal of Pharmaceutical Sciences*, Vol. 88, No. 8, p. 815 (1999) and Winiwarter, et al. Correlation of Human Jejunal Permeability (in Vivo) of Drugs with Experimentally and Theoretically Derived Parameters. A Multivariate Data Analysis Approach, *Journal of Medicinal Chemistry* 41, p. 4939 (1998), both of which are hereby incorporated by reference in their entireties.

Although these models have improved the speed of the drug candidate evaluation process by reducing reliance on in vivo and in vitro chemical testing, they remain computationally expensive, and in many cases, the strict linear modeling limits their predictive value. PSA calculations have required the calculation of energy minimized three dimensional molecular structures, which requires 10–15 seconds of CPU time on a Sun or SGI-R1000 workstation. The effective application of these techniques to large libraries of candidate compounds requires techniques which reduce the computation time required for each molecule.

SUMMARY OF THE INVENTION

In one embodiment, the invention comprises a method of estimating the polar surface area of a molecule comprising making separate counts of the number of atoms or atom clusters in the molecule which fall within the definition of each of a plurality of atomic classes, and estimating a polar surface area of the molecule using at least some of the separate counts.

Computed polar surface areas are useful in computer implemented compound analysis methods, and the invention also comprises a method of predicting the propensity of a molecule for membrane permeability comprising computing a polar surface area for the molecule without reference to an energy minimized three dimensional structure of the molecule and using the computed polar surface area to predict the propensity.

Methods of drug discovery are also provided. In one embodiment, such a method comprises selecting a subset of molecules from a database, wherein the selecting comprises numerically estimating the PSA and logP of each molecule in the database, determining the position of each compound in the database in a PSA-logP plane, and categorizing compounds based on their position on the PSA-logP plane.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In many embodiments, the invention is useful in the computer implemented drug candidate evaluation process. In these processes, drug candidates from one or more databases of compounds are preliminarily evaluated using software code running on general purpose computers for desirable characteristics or properties. The general purpose computers used for this purpose can take a wide variety of forms, including network servers, workstations, personal computers, mainframe computers and the like. The code which configures the computer to perform these compound evaluations is typically provided to the user on a computer readable medium such as a CD-ROM. The code may also be downloaded by a user from a network server which is part of a local or wide area network such as the Internet.

The general purpose computer running the software will typically include one or more input devices such as a mouse and/or keyboard, a display, and computer readable memory media such as random access memory integrated circuits and a hard disk drive. It will be appreciated that one or more portions, or all of the code may be remote from the user and, for example, resident on a network resource such as a LAN server, Internet server, network storage device, etc. In typical embodiments, the software receives as an input a variety of information concerning candidate drug compounds or compositions, and from this information, derives, estimates, or predicts the expected biological or chemical characteristics of the candidate drug compounds. The databases may include 10,000, 100,000, or possibly more candidate compounds. In some advantageous embodiments, the information input to the software program comprises structural information about each of the candidate compounds. This information is usually limited to the atomic constituents and the bonds between them, essentially the information found in a 2-dimensional molecular bonding diagram. From this information, predictions of biological and/or chemical activity are advantageously made.

As discussed above, it is desirable to predict which compounds in a database are likely to be readily intestinally absorbed, or are likely to penetrate the blood-brain barrier. As also described above, the molecular polar surface area is often used as part of this prediction. In conventional methods of polar surface area calculation, the atomic constituents and interatomic bond configurations are used to generate energy minimized 3-dimensional molecular structures using well known molecular modeling tools. These calculations may be performed in vacuum or in solution. After 3-dimensional structures are calculated, the PSA is defined as the portion of van der Waals surface area of all oxygen atoms, nitrogen atoms, and their attached hydrogen atoms which does not lie within the van der Waals surface area of any other atom, where the van der Waals surface is defined by the space filling hard sphere having the van der Waals radius for the atom type. Thus, the total amount of "exposed" oxygen, nitrogen, and associated hydrogen of the molecule defines the PSA.

The conventional PSA calculation is useful in the process of predicting intestinal absorption. However, the generation of energy minimized three dimensional molecular structures is computationally difficult and time consuming. Calculating PSA for every compound in a 100,000 compound combinatorial library would take anywhere from 10–20 days of computer time on widely used workstations.

Figure 1:
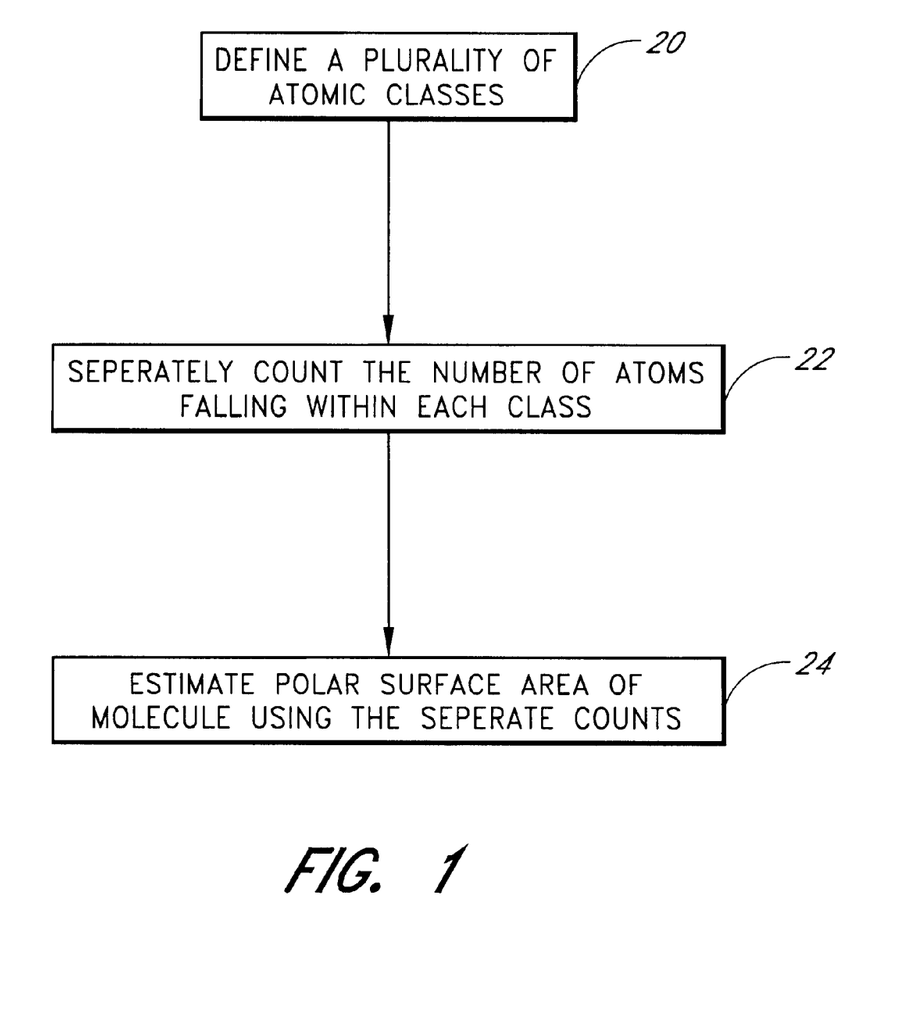
FIG. 1 is a flowchart of a method of calculating polar surface area in accordance with one embodiment of the invention.

It is one aspect of the present invention that PSA may be calculated by an atom and atom cluster classification method that speeds the calculation by a factor of 300 to 1000, making it possible to compute PSA for each molecule of a 100,000 molecule database in less than an hour. This process is illustrated in FIG. 1.

Referring now to this Figure, the method begins at block 20 by defining a plurality of atomic classes. Each atomic class may comprise a single atom or a cluster of atoms. Each class is also typically defined by bond configurations within the cluster and/or to other atoms. For example, an atomic class may comprise "a double bonded oxygen atom," "a single bonded $NH_2$ group," and the like. In the present embodiment, the classes involve nitrogen atoms, oxygen atoms, and attached hydrogen atoms, as these molecular constituents are the ones that contribute to the molecule's PSA. At block 22, the number of atoms or atom clusters of a molecule being analyzed that fall within each defined class are separately counted, thus producing a list of integers corresponding to the number of atomic constituents within each defined class. As illustrated by block 24 of FIG. 1, the separate counts are used to estimate the polar surface area of the molecule being evaluated. In one advantageous embodiment described in additional detail below, the counts are used in a simple arithmetic calculation which produces an estimated PSA value. Therefore, rather than calculating PSA by computing the van der Waals surface areas of relevant atoms of an energy minimized three dimensional molecular structure, a simple computation is used which takes far less computation time.

In an especially advantageous embodiment, the PSA is expressed as a linear equation with non-negative coefficients as follows:

$$PSA = \Sigma_i C_i N_i \qquad (1)$$

where $N_i$ is the number of atoms or atom clusters in the molecule falling within class i, and $C_i$ is a coefficient associated with class i. In this model, the coefficients represent the contribution of each atom type to the total PSA of a molecule. The coefficients are all non-negative because the classes include all polar atoms and atom clusters that tend to add to molecular PSA. Coefficients for the above formula may be computed by performing a non-negative least squares linear regression using a plurality of training molecules. This technique is well known in a few other applications, with the prediction of boiling point for organic molecules being one example. Hall and Kier, Electrotopological State Indices for Atom Types: A Novel Combination of Electronic, Topological, and Valence State Information, *J. Chem. Inf. Comput. Sci.* Vol. 35, 1039–1045 (1995), hereby incorporated by reference in its entirety. The procedure for generating the coefficients is to select a set of training molecules, and compute all of their PSA values the conventional way, by calculating energy minimized three dimensional structures and computing the van der Waals surface areas of nitrogens, oxygens, and their attached hydrogens. Then, counts of the atoms or atom clusters of each class are made for each molecule. The coefficients are then computed such that the sum of the squares of the PSA errors computed with the above formula is minimized across all of the molecules of the training set with the constraint that the each of the regression coefficients be greater than zero.

These methods have never been applied to the calculation of polar surface area, or any other calculated (as opposed to experimentally measured) quantities, prior to the present invention. Other closely related surface-area quantities, such as the total surface area or the non-polar surface area, can vary considerably with changes in conformation. In contrast, the surprising accuracy of the PSA model set forth above throughout a wide range of PSA values indicates that the polar surface area for solvated conformations is considerably less dependent on the conformation than are these related measures. Only under those circumstances is it possible to identify a set of bonded states of the heteroatoms of the molecule forming a suitable basis for the regression calculation.

Table I below sets forth a list of atomic classifications and associated coefficients in one embodiment of the invention.

TABLE I

| Atomic Classification | Atom/Atom Cluster | Linear Coefficient |
|---|---|---|
| sNH3<br>single bonded $NH_3$ | —$NH_3$ | 32.254 |
| sNH2<br>single bonded $NH_2$ | —$NH_2$ | 26.54 |
| ssNH2<br>$NH_2$ with two single bonds |  | 0 |
| dNH<br>double bonded NH | =NH | 23.0878 |
| ssNH<br>NH with two single bonds |  | 12.8102 |
| aaNH<br>aromatic NH |  | 15.0551 |
| tN<br>triple bonded N | ≡N | 22.9351 |

TABLE I-continued

| Atomic Classification | Atom/Atom Cluster | Linear Coefficient |
|---|---|---|
| sssNH<br>NH with three single bonds |  | 3.204 |
| dsN<br>N with double and single bond | =N— | 11.3233 |
| aaN<br>aromatic N |  | 11.261 |
| sssN<br>N with three single bonds |  | 3.3525 |
| ddsN<br>N with two double bonds and one single bond | =N— | 8.2215 |
| aasN<br>aromatic N with single bond |  | 5.3483 |
| ssssN<br>N with four single bonds |  | 0 |
| sOH<br>single bonded OH | —OH | 20.8155 |
| dO<br>double bonded O | =O | 17.3008 |
| ssO<br>O with two single bonds | —O— | 8.9301 |
| aaO<br>aromatic O |  | 12.5543 |

These coefficients were produced by calculating the PSA explicitly using energy minimized three dimensional structures for the 5,386 most drug like molecules contained in the Comprehensive Medicinal Chemistry (CMC) Database using a single extended conformer, not multiple conformers. The molecules were separated into training, test, and validation datasets. The validation dataset consisted of the 440 molecules which are listed in the Physician's Desk Reference as currently available pharmaceuticals in tablet, capsule, or oral suspension form. Compounds listed in the validation dataset were removed from the CMC dataset prior to the creation of the training and test datasets, so as to not bias the regression. The training and test datasets were created by sorting the remaining molecules from the CMC in the order of their explicitly calculated PSA value, and assigning odd molecules to the training dataset and even molecules to the test dataset. This created two datasets spanning equal PSA range. Counts of each of the 18 atomic classifications set forth above in Table I were made for each molecule. The counts for the molecules in the training dataset were used as independent variables in the linear equation of the form set forth above in formula (1). Coefficients were derived using conventional and well known non-linear least squares regression techniques so as to minimize the total error between predicted PSA using the linear equations and calculated PSA from energy minimized three dimensional structures. The coefficients were limited to non-negative constants, and the intercept was fixed to zero.

Figure 2:
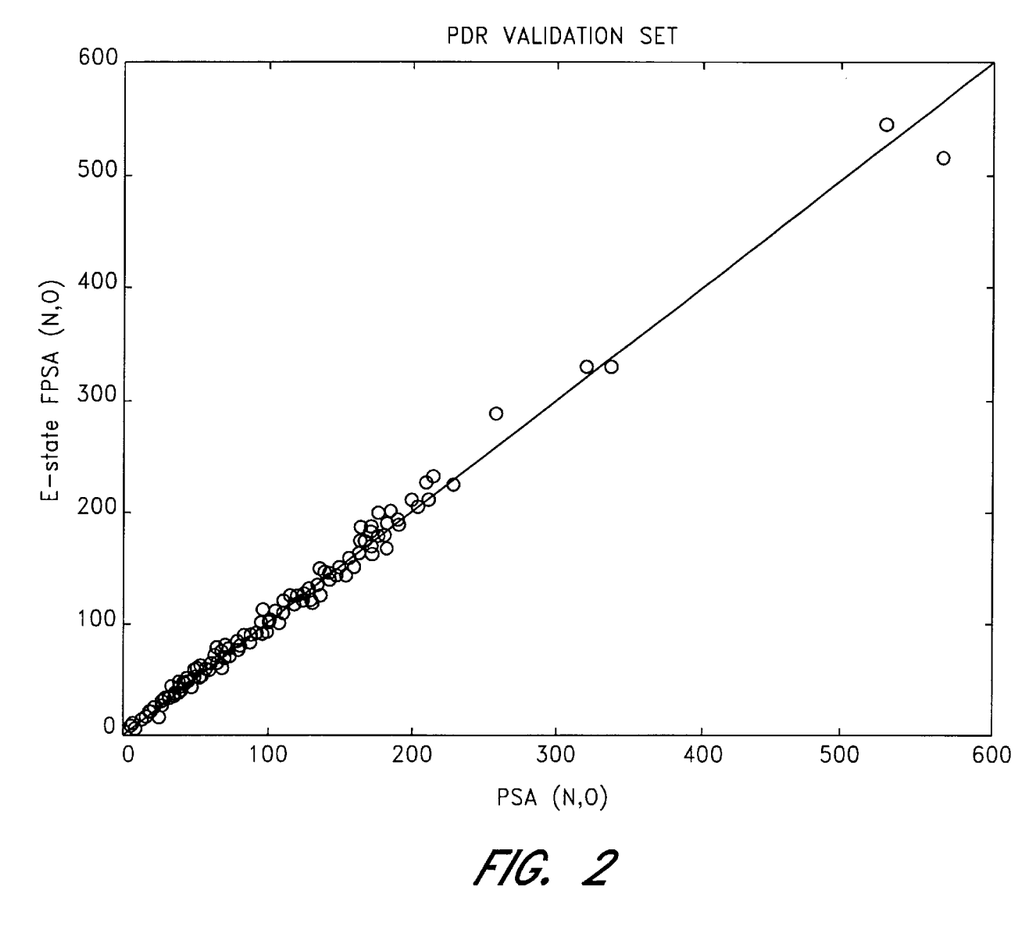
FIG. 2 is a plot of estimated versus calculated polar surface areas for 440 compounds from the Physician's Desk Reference.

FIG. 2 is a scatter plot of estimated PSA using formula (1) above and the coefficients of Table 1 vs. PSA calculated with three dimensional structures for the validation dataset. Agreement between arithmetically estimated and structurally calculated PSA is very good, with $R^2>0.991$, and a root-mean-square PSA error when using the fast calculation method of formula (1) of only 5.9 square angstroms. The speed of calculation is anywhere from twenty to over a hundred molecules per second when using arithmetic formula (1) and the atomic classifications and coefficients of Table 1. This is a dramatic improvement over the 10–15 second per molecule for conventional PSA calculation methods using energy minimized three dimensional structures.

Due to the large improvement in computation speed, the above described method of PSA calculation can be advantageously applied to the evaluation of candidate drugs in large compound databases for their propensity for intestinal absorption. Using the principles of the invention described above, three dimensional structures of the compounds need not be generated to compute PSA, thereby speeding the process of evaluating candidate drugs dramatically. For example, one proposed method referred to above for selecting compounds likely to be well absorbed biologically is to compare the PSA to the threshold value of 140 square angstroms. According to this model, compounds above this threshold are likely to be poorly absorbed. Using a linear equation for PSA calculation such as formula (1) above, a 100,000 compound library could be screened and all compounds likely to be poorly absorbed could be separated from the remainder in less than an hour of computation time with workstations currently in widespread use for these applications.

Other models have been proposed for identifying compounds which are likely to be poorly absorbed. Some of these models include consideration of both molecular PSA and molecular octanol/water partition coefficient, logP. It has long been known that logP, although it can be determined experimentally, is also well modeled by linear equations of the same form as formula (1) above. Thus, in the evaluation of molecules of a database, logP can be estimated based on counts of atoms or atom clusters in various atomic classifications and associated multiplicative coefficients. Two linear models, known as ALOGP and CLOGP to those of skill in the art, are widely used. See, e.g. Ghose, et al., prediction of Hydrophilic (Lipophilic) Properties of Small Organic Molecules Using Fragmental Methods: An Analysis of ALOGP and CLOGP Methods, *Journal of Physical Chemistry A*, Vol. 102, 3762–3772, incorporated herein by reference in its entirety.

The molecular parameters PSA and logP are relevant descriptors of intestinal absorption and logBB. This is because passive diffusion into the intestine or through the blood-brain barrier requires diffusion of the molecule through cellular membranes comprising a lipid bilayer with both hydrophilic and lipophilic regions. Accordingly, highly hydrophilic molecules and molecules which readily form hydrogen bonds do not easily enter the membrane. Furthermore, highly lipophilic molecules do not readily leave the membrane once reaching the lipophilic interior. PSA, being a measure of hydrophilicity, and logP, which includes both hydrophilic and lipophilic contributions, have thus been found to be parameters from which membrane permeability information may be derived.

The relationships between PSA and logP to membrane permeability, however, are highly non-linear. As described above, extremes of high and low logP are associated with poor intestinal absorption. Molecular PSA shows a sigmoidal relationship to intestinal absorption. If accurate bioabsorption data for a significant portion of chemical space were available, an accurate non-linear model would be derivable which could predict numerically measured intestinal absorption and/or logBB properties of candidate drugs with sufficient accuracy. Because such data is unavailable, a novel modeling technique, based on PSA and logP values, has been developed, and is described below with reference to FIGS. 3–5. In accordance with this aspect of the invention, it has been found that a statistically based pattern recognition model based on PSA and logP, rather than a standard quantitative model is surprisingly successful at distinguishing well absorbed from poorly absorbed compounds.

In accordance with one aspect of the invention, the model assumes that a molecule's propensity for intestinal absorption via passive diffusion is a function of the PSA and logP of the molecule, especially the interactions between PSA and logP. Every molecule may be thus assigned a location in a two dimensional PSA-logP plane. Rather than quantitatively predicting intestinal absorption as a function of position in the PSA-logP plane, a bounded region of the PSA-logP plane is defined. If the PSA and logP of a molecule are within the bounded region, the molecule is considered likely to be readily intestinally absorbed. If the PSA and logP of a molecule are outside the bounded region, the molecule is considered unlikely to be readily intestinally absorbed. To define this bounded region of high intestinal absorption within the PSA-logP plane, a statistical analysis of compounds which are known to be readily absorbed was performed. The PSA and logP for 182 compounds known to be readily absorbed and not actively transported across cellular membranes were calculated. The distribution of (PSA, logP) coordinates for these molecules was analyzed statistically assuming a multivariate normal distribution.

Figure 3:
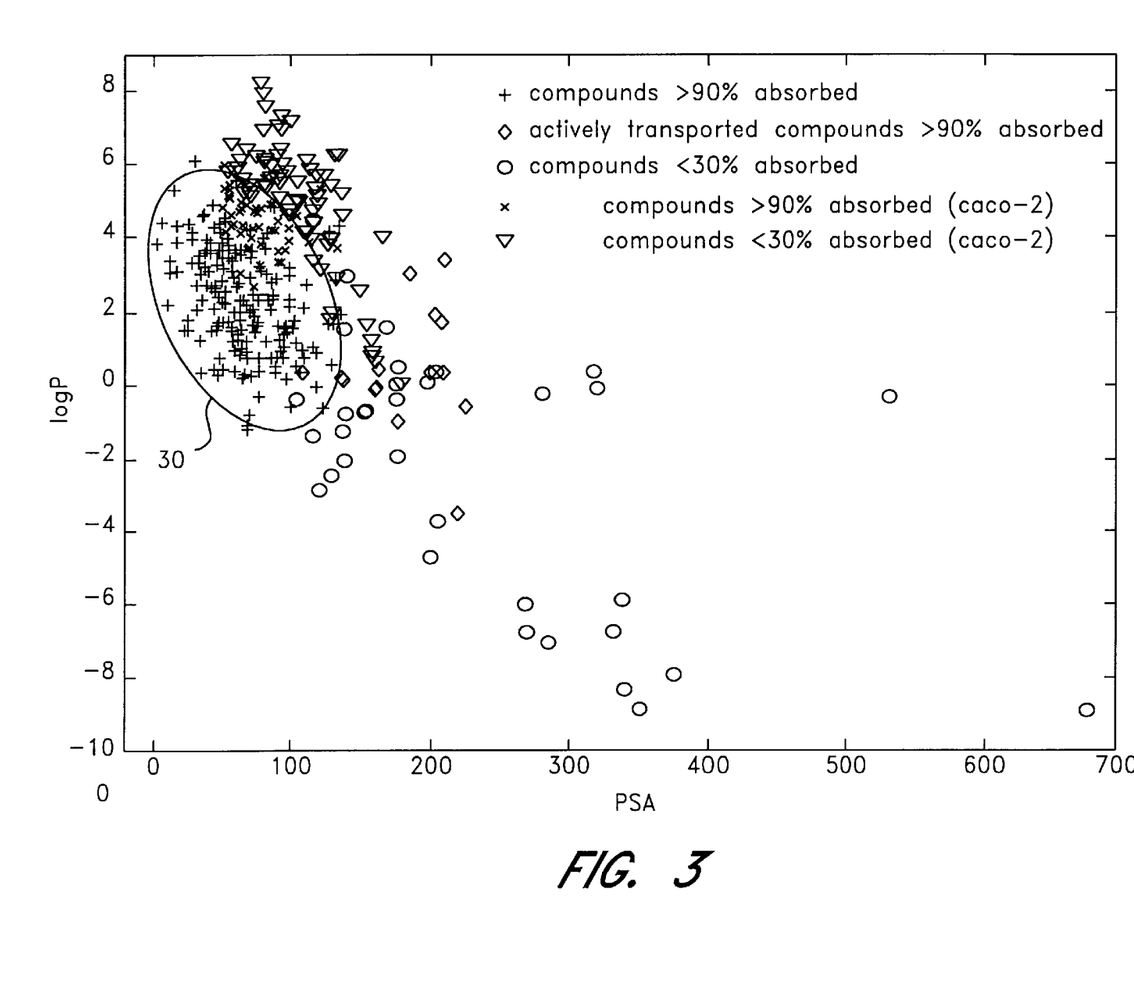
FIG. 3 is a scatter plot of compounds in a PSA-logP plane including a statistically defined boundary between readily absorbed compounds and poorly absorbed compounds.

FIG. 3 illustrates the distribution in the PSA-logP plane of known readily absorbed compounds which are illustrated with "+" symbols in this Figure. The mean PSA of these molecules is 64.5867, and the mean logP is 2.3226. Broadly stated, the model predicts that new molecules being analyzed which have a PSA and logP "close" to these mean values will also be readily absorbed, and that new molecules being analyzed which have a PSA and logP "far" from these mean values will not be readily absorbed. To define how close is close enough, the model utilizes Hotelling's $T^2$ distance as a reference to measure distance from the mean values. The boundary 30 illustrated in FIG. 3 is the 95% confidence region for the Hotelling's $T^2$ distance calculated using standard statistical analysis of the data points provided by the known readily absorbed compounds.

The coefficients required to compute the $T^2$ distance for compounds are determined as follows: 1) compute the average PSA and logP for a selected set of well absorbed compounds. 2) mean center the individual values of PSA and logP for each of these compounds (subtract the average values), 3) decompose this mean-centered dataset with any algorithm which provides numerically stable eigenvalues and eigenvectors (the singular value decomposition (SVD) may be used, giving standard U, S, and V output matrices). Compute the $T^2$ distance (also known as the squared Mahalanobis distance) for any compound(s), new or those used in the model creation, using the average values and SVD results (or eigenvalues/eigenvectors from some similar method) to perform the transformations given by mean centering and multiplication by the covariance matrix, per Rencher, *Methods of Multivariate Analysis,* John Wiley & Sons, Inc.: New York, 1995, hereby incorporated by reference in its entirety. The confidence region/probability of a compound's similarity to well absorbed compounds may be computed using the F-distribution relationship to $T^2$, per Rencher.

For the distribution of readily absorbed compounds of FIG. 3, the $T^2$ distance from the mean is computed as follows:

$$T^2=(181)*\text{diagonal}((A*B)*(A*B)^T) \quad (2)$$

where A and B are the matrices:
A=[PSA-64.5867 logP-2.3226] and $$B = \begin{bmatrix} 0.00274246014581 & -0.00114013550277 \\ -0.00005529017061 & -0.05655211663560 \end{bmatrix}$$

If the $T^2$ distance calculated in this manner is greater than 6.126, the compound falls outside the 95% confidence region, the boundary 30 of FIG. 3 in the PSA-logP plane, and is predicted by the model to be poorly absorbed.

The model may be tested by plotting (PSA, logP) datapoints for additional molecules known to be poorly absorbed. These are shown as open circles on FIG. 3, and it is immediately apparent that almost all of them fall outside the boundary 30. Further verification of model validity is available by plotting molecules which show high membrane permeability or low membrane permeability in caco-2 cell assays, a commonly used in vitro assay for intestinal permeability. In FIG. 3, molecules which show high caco-2 permeability are plotted with "x" symbols, and molecules which show low caco-2 permeability are plotted with open triangles. It can be seen that the high permeability molecules fall predominantly within the boundary 30, and low caco-2 permeability molecules fall predominantly outside the boundary 30. Comparison of the $T^2$ distances and their associated probabilities with in vitro data reveals that the permeability through caco-2 cell membranes drops sharply as the compounds move outside the 95% probability region.

One important aspect of this method is that the multivariate normal distribution permits estimation of the probability that a compound is similar to specified reference compounds which are well absorbed. As a molecule moves farther away from the centroid of the PSA-logP space, its probability of being similar to well absorbed molecules decreases. The model as shown in FIG. 3 uses "either/or" logic, characterizing a molecule as being well or poorly absorbed by comparing its $T^2$ distance to a threshold. However, it may also be noted that the base calculation of $T^2$ distance, which is computed first, is one measure of the probability of a molecule's similarity to well absorbed compounds. Thus, the model may not only be used to categorize molecules as simply well or poorly absorbed, but may be used to quantify the probability that a compound will have absorption characteristics similar to the set of known readily absorbed compounds. In the latter case, compounds in a database can be ordered according to their likelihood of having similar absorption properties to well absorbed compounds. This ordering can in turn be used to prioritize compounds for synthesis and screening.

An improved numerical formula for calculating a predicted logBB may also be developed based on the statistical model set forth above. It has been shown that logBB is modeled with reasonable accuracy with a linear formula having PSA and logP as variables. Clark, supra. However, an unbounded linear model like the one proposed by Clark can be improved by restricting its application to compounds that fall within the boundary 30 of FIG. 3. Penetration of the blood-brain-barrier is known to be more difficult than intestinal absorption, and the rapid drop in caco-2 permeability seen near the boundary 30 of FIG. 3 suggests that this is a likely point at which linearity is significantly lost. Least-median-of-squares linear regression was used to compute a robust linear regression whose coefficients are different from those set forth by Clark, and an improved linear model is produced having an $R^2$ of 0.861 rather than Clark's 0.787. Furthermore, the boundary 30 was used as a second criterion to deal with the non-linearity of the permeability, and any predictions for logBB made by the linear regression are considered invalid if the molecule is outside boundary 30. Thus, this logBB model does not numerically predict logBB for compounds that fall outside the region of FIG. 3, but predicts qualitatively that such compounds will poorly penetrate the blood-brain barrier. A linear regression performed according to these principles produces the following formula for logBB:

$$\text{logBB}=-0.01577*(\text{PSA})+0.217697*(\text{logP})+0.119233 \quad (3)$$

Figure 4:
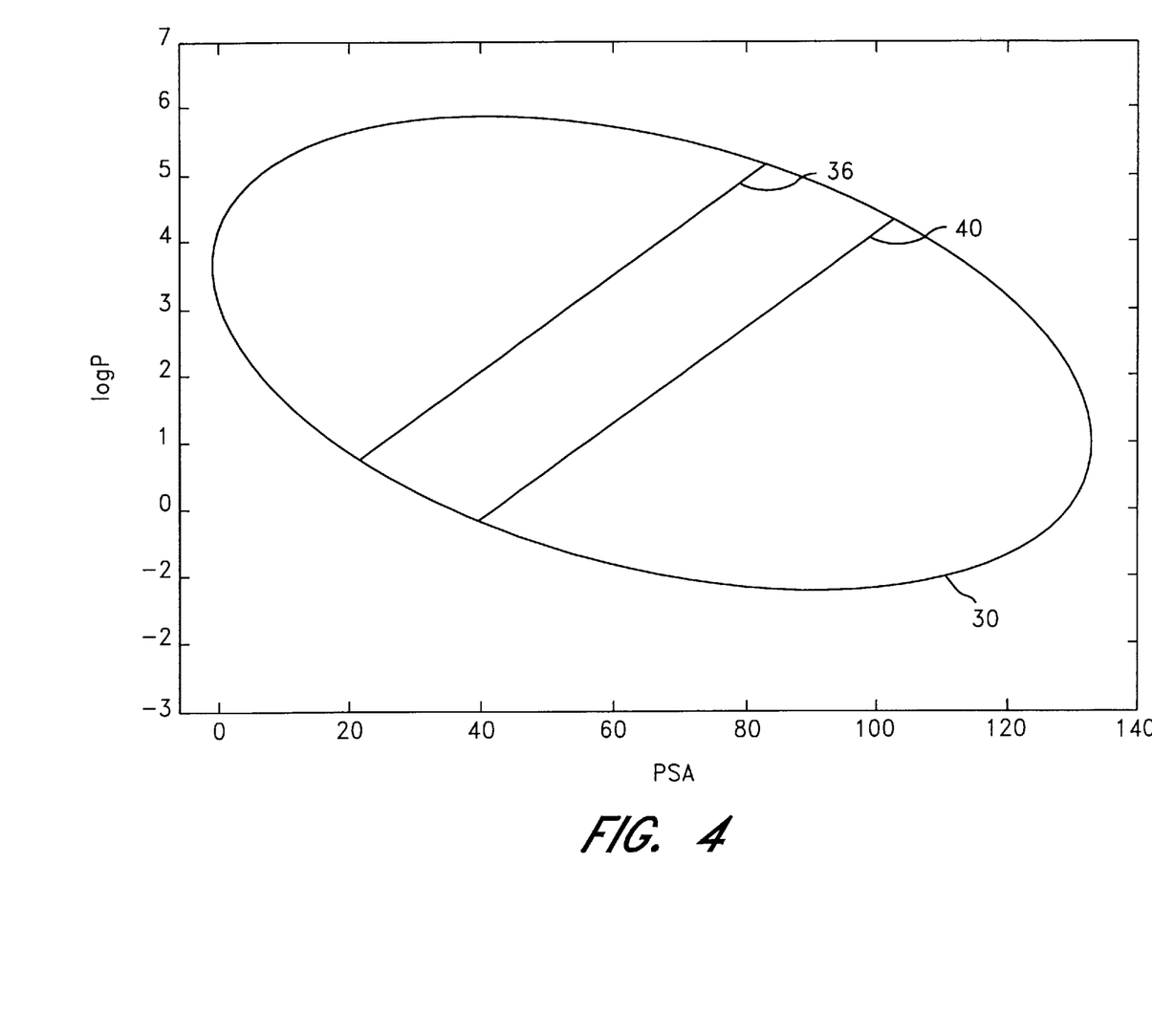
FIG. 4 is another scatter plot of compounds in a PSA-logP plane showing the boundary of FIG. 3 and regions of chemical space having predicted high logBB and low logBB.

This is illustrated graphically in FIG. 4. Compounds residing in the PSA-logP plane within the boundary 30 and to the left of line 36 are predicted to have a BB of greater than 1 (i.e. logBB of greater than 0), and compounds residing in the PSA-logP plane within the boundary 30 and to the right of line 40 are predicted to have a BB of less than 0.5.

The above described model has a variety of advantages over conventional absorption prediction techniques, especially when applied to the evaluation of large libraries of compounds. The model may be used advantageously no matter how PSA and logP are derived for candidate compounds. However, using the linear arithmetic PSA calculation described above, both PSA and logP can be calculated using linear sums of counts of atoms and atom clusters within each molecule that fall within defined atom classifications, resulting in far lower computation times. Furthermore, qualitative predictive accuracy is also improved. Thus high quality and extremely fast chemical database screening may be performed with the principles of the invention.

Figure 5:
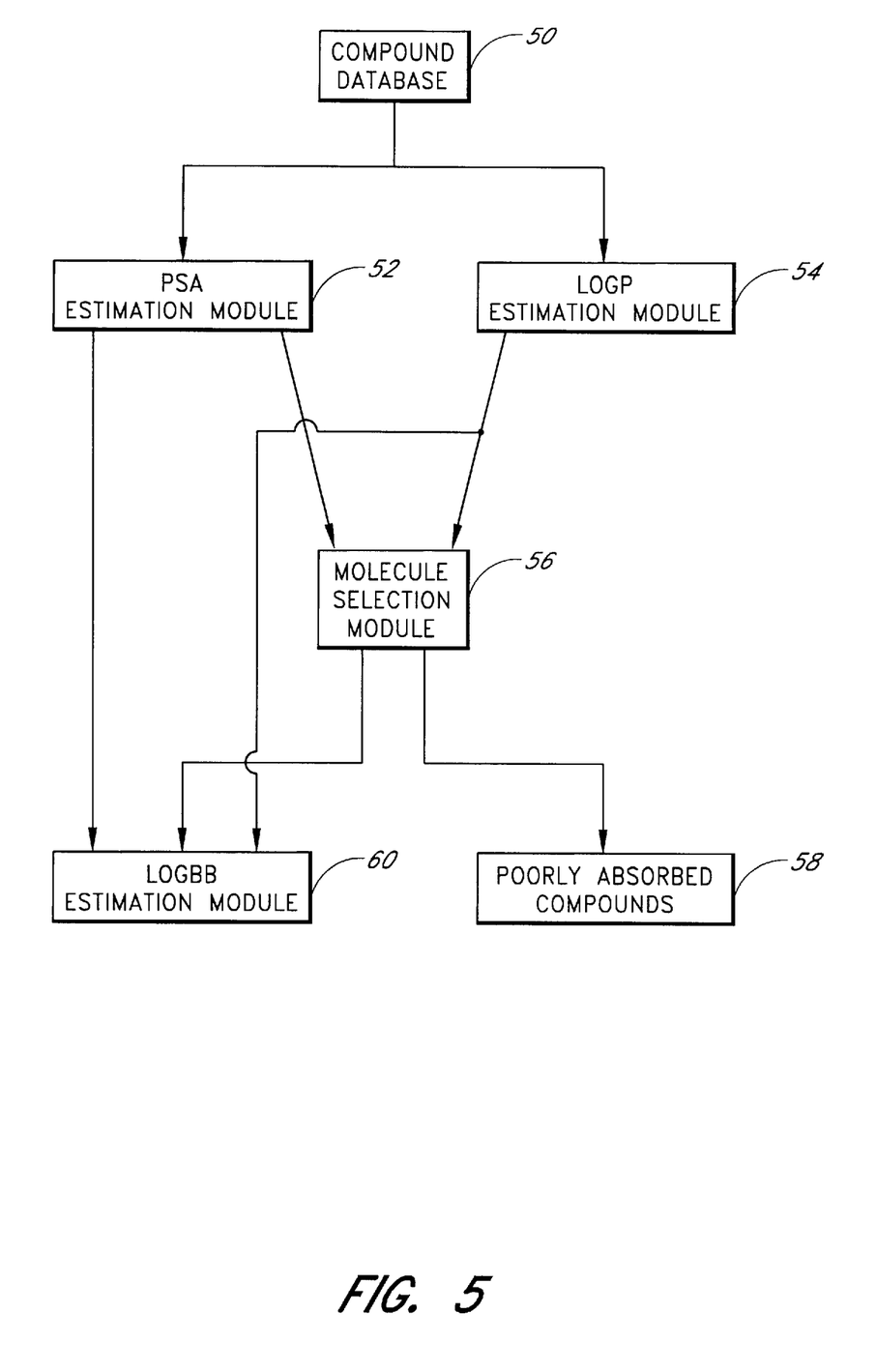
FIG. 5 is a block diagram of a drug discovery system in one embodiment of the invention.

FIG. 5 illustrates a computer implemented molecule screening system in accordance with one embodiment of the invention. In this system, information about the atomic constituents and associated bonds is retrieved from a compound database 50. This information is routed to a PSA estimation module 52 and a logP estimation module 54. In some advantageous embodiments, PSA is calculated using a linear equation as set forth in formula (1), and uses the coefficients from Table 1. LogP may be estimated using a variety of known methods, including the ALOGP or CLOGP methods. The estimated PSA and logP values are then forwarded to a molecule selection/categorization module 56. This module 56 categorizes compounds of interest in accordance with their probability similarity to well absorbed molecules. The module 56 may separate candidate molecules as being within or outside the boundary 30 of FIG. 3 using formula (2) above, and may also order compounds according to their probability of showing similarities to well absorbed compounds based on their distance from the centroid of well absorbed compounds in the PSA-logP plane.

Compounds predicted to be poorly absorbed 58 may be separated out. If desired, PSA and logP values for some compounds may be routed to a logBB estimation module 60, which numerically calculates logBB for desired molecules using linear formula 3 above.

The invention serves the broad purpose of prioritizing candidate molecules. Candidate molecules existing only in a virtual sense may be prioritized for synthesis, while candidate molecules which have been synthesized may be prioritized for screening. Furthermore, this process may be iterated numerous times. After synthesis and screening, in vitro and/or in vivo absorption data is produced, creating a new data point which may be added to model. New information gained during the drug discovery process may thus be used to improve the model and thus the synthesized compounds.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of predicting absorption of a molecule comprising:

numerically estimating Polar Surface Area and logP of the molecule;

determining a position of the molecule in a two-dimensional plot of Polar Surface Area against logP;

determining a distance between the position of the molecule on said plot and a centroid of a pre-defined region of the plot; and predicting absorption of said molecule based on said distance.

2. The method of claim 1 additionally comprising prioritizing said molecule for synthesis and/or screening based on its distance from the centroid.

3. The method of claim 1, wherein numerically estimating Polar Surface Area comprises:

defining a plurality of atomic classes;

making separate counts of the number of atoms in said molecule which fall within the definition of each of said classes;

estimating a Polar Surface Area of said molecule using at least some of said separate counts.

4. The method of claim 1 comprising predicting passive intestinal absorption.

5. The method of claim 1 wherein the pre-defined region is mathematically defined by Hotelling's $T^2$.

6. The method of claim 1 wherein determining the distance comprises determining Mahalanobis distance.

* * * * *